United States Patent
Vuong

(10) Patent No.: US 8,668,942 B2
(45) Date of Patent: Mar. 11, 2014

(54) SKIN ANTI-OXIDANT ENHANCING FORMULATION AND ASSOCIATED METHOD

(71) Applicant: Le Thuy Vuong, Petaluma, CA (US)

(72) Inventor: Le Thuy Vuong, Petaluma, CA (US)

(73) Assignee: Fishrock Laboratories, Inc., Davis, CA (US)

( * ) Notice: Subject to any disclaimer, the term of this patent is extended or adjusted under 35 U.S.C. 154(b) by 0 days.

(21) Appl. No.: 13/897,297

(22) Filed: May 17, 2013

(65) Prior Publication Data

US 2013/0309183 A1 Nov. 21, 2013

Related U.S. Application Data

(60) Provisional application No. 61/688,616, filed on May 18, 2012.

(51) Int. Cl.
*A01N 65/00* (2009.01)
(52) U.S. Cl.
USPC ........................................................ 424/725
(58) Field of Classification Search
None
See application file for complete search history.

(56) References Cited

U.S. PATENT DOCUMENTS

2009/0110789 A1* 4/2009 Mower et al. .............. 426/330.5

* cited by examiner

*Primary Examiner* — Michael Meller

(57) ABSTRACT

The present invention describes novel applications of an oil formulation rich in carotenoids and poly-unsaturated fatty acids (PUFA) for skin care, lip care and cosmetic use. The formulation contains natural oil extract of *Momordica cochinchinensis* Spreng also known as gac, spiny melon, Redmelon™. The formulation contains carotenoid antioxidants (beta-carotene and lycopene), pro-vitamin A carotenoid (alpha and beta-carotene), and vitamin E. In addition, the formulation contains omega-3, omega-6, omega-9 fatty acids, the essential fatty acids important in enhancing skin integrity, elasticity. The oil-based formulation helps skin to retain water, Carotenoids in the formula protects skin from oxidative damage. The novelty of this invention is in the mixture of antioxidants, retinol and essential fatty acids to deliver a stable, bioavailable and nutritious composition for skin care. In addition, the formulation provides vitamin E and retinol beneficial in skin therapeutic and cosmetic applications.

1 Claim, 1 Drawing Sheet

SKIN ANTI-OXIDANT ENHANCING FORMULATION AND ASSOCIATED METHOD

1. PARENT CASE TEXT AND RELATED APPLICATION

Figure 1A:
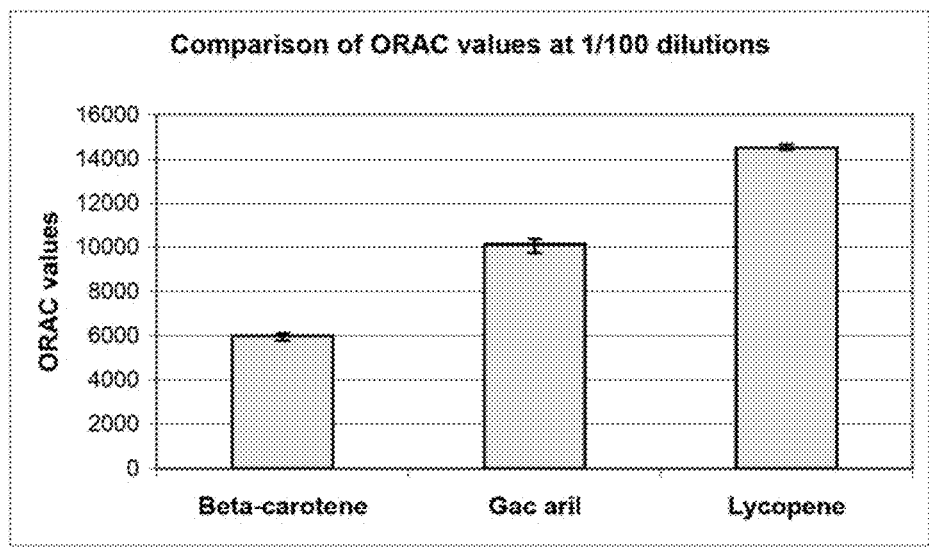

This application claims priority from U.S. provisional patent No. 61/688,602 filed May 18, 2012, the contents of which are to be taken as incorporated herein by this reference.

2. FIELD OF INVENTION

This invention relates to formulations and methods for applying a mixture of carotenoid antioxidants in an oil form to enrich skin of a subject. Accordingly, the invention involves the fields of botany, nutritional, skin care, cosmetics, nutraceuticals, and natural ingredients.

3. OBJECTS AND ADVANTAGES

The novelty of this invention is in the mixture of antioxidants, retinol and essential fatty acids to deliver a stable, bioavailable and nutritious composition for skin care. The formulation is a combination of carotenoid antioxidants, in an oil form, and thus more stable. Another novelty is that the oil is rich in essential fatty acids, thus skin integrity can be enhanced, as well as protected. The oil contains natural preservative (alpha-tocopherol) therefore stable. The composition also delivers a plant-based retinol to help with new skin generation, at the same time non-toxic. This invention provides a safe and nutritious formulation for protecting and treating skin oxidative damage. The composition is low water activity and thus has a long shelf life.

4. SUMMARY OF INVENTION

This invention describes a lipid-base composition containing antioxidant carotenoids, alpha-tocopherol, plant-based retinol and essential fatty acids to be used in the formulation of skin care products. In particular, a method to deliver highly absorbed and stable lycopene and beta-carotene to protect and enrich skin is provided. The formulations and associated method are characterized by the effective amount of oil extract from *Momordica cochinchinensis* Spreng, containing antioxidant carotenoids and a lipid profile which enhance skin integrity, plus vitamin E, synergistically provide bioavailable and stable antioxidants. The formulations contain a non toxic plant-based retinol that can be administered topically or orally.

5. BACKGROUND AND PRIOR ART

Skin is the first defense of the body from infection. Skin is damaged by exposure to sun, UV light (photo damaged), by aging; and thus efforts have been continued to find compositions to protect and nourish skin, and reduce the effect of aging. The roles of carotenoids in humans health are well studied and documented (Cooper, 2004). Several carotenoids show enhancement of the immune response, inhibition of mutagenesis, reduction of induced nuclear damage, and protection from various neoplastic events in cells, tissues, and whole body. Carotenoids also protect against photo-induced tissue damage. Some carotenoids quench highly reactive singlet oxygen under certain conditions and can block free radical-mediated reactions (Olson, 1999). They are named antioxidant carotenoids. Carotenoids as potent antioxidants have been reported by numerous scientists (Krinsky N., Antioxidant functions of carotenoids. Free Radical Biology & Medicine, Vol. 7, pp. 617-35, 1989.). The use of plant-carotenoids against skin damage has been reported by Weiss, Stahl, W. and other workers (Stahl, W. Carotenoids and flavonoids contribute to nutritional protection against skin damage; Mol. Biotechnol. 37(1):26-30, 2007; Stahl, W. Lycopene-rich products and dietary photoprotection. Photochem Photobiol. Sci. 5(2): 238-42, 2006; "Carotenoids and protection against solar UV radiation" in Skin Pharmacol App. Skin Physiol, 15(2): 291-6, 2002); Stahl, W. "Tomato Paste protects against ultraviolet light-induced erythema in humans". J. Nutr. 131 (5): 1449-51, 2001; Cesarini, J P, "Immediate effects of UV radiation on the skin: modification by an antioxidant complex" Photodermatol Photoimmunol Photomed. 19(4):182-9, 2003; Protection against ionizing radiation by antioxidant nutrients." Toxicology 189(1-2): 1-20, 2003).

β-Carotene and lycopene are among the most prominent members of this group of carotenoid antioxidants. In addition, beta-carotene is among carotenoids having vitamin A activity, meaning they can be cleaved enzymatically in the body to yield vitamin A. In theory, one molecule of beta-carotene can be cleaved enzymatically to produce two molecules of retinol. Retinol has been shown to be effective in reducing effect of skin damage. Synthetic retinol is toxic when taken a large dose, and is not commended for children or pregnant women, however pro-vitamin A carotenoids, have not been found to be toxic.

Carotenoids are very susceptible to oxidation and heat, and will react with oxygen in the air to render them inactive and colourless.

Carotenoids are lipid soluble and thus stable in lipid medium. Carotenoids when present with other antioxidants such as vitamin E, vitamin C, are more stable due to the "sparing effect".

Essential fatty acids, such as omega-3, omega-6, omega-9 are not produced by the body however essential for immune response, and skin health. Oil containing high concentrations of essential fatty acids provides a stable vehicle to deliver carotenoids also enhances integrity of skin.

*Momordica cochinchinenensis* is a variety of melon indigenous to south East Asia. This fruit is also known as "Gac" (in Vietnam). The seed pulp of the fruit contains high concentration of beta-carotene and lycopene. A natural process of extracting carotenoids from the seed pulp has been published by Vuong. Extraction of carotenoids by chemical solvents has been described by Ishida et al. Both methods are listed subsequently.

A method using no chemicals to extract beta-carotene from *mormordica cochinchinensis* (gac fruit) was described by Vuong in U.S. Pat. No. 6,770,585 filed Aug. 2, 2002. This patent claimed a process to produce an oil rich in carotenoids to be used as a safe source of dietary supplement of vitamin A for children and pregnant women in rural areas of developing countries.

A process patent filed subsequently by Ishida et al. (U.S. Pat. No. 7,572,468 by filed Aug. 11, 2009) showed a process using chemical solvent to extract carotenoids from plant material including "gac" fruit.

Due to the high concentrations of carotenoids, its use in dietary supplement has been published (Smidt et al.). Mower et al. described the use of *momordica cochinchinensis* puree as a sweetener, to mask the bitterness of other phytonutrients in the composition. In U.S. Pat. No. 5,942,233 by Chang, Teh Shan filed on Aug. 24, 1999 titled "Herbal composition for stimulating blood circulation". This invention described the use of *momordica cochinchinensis* as one of the components in a paste that is useful for re-establishing of vital energy, invigorating of blood circulation. None of those patents described the use of components from the oil extract from "gac" to moisten, and protect skin.

Foreign inventions filed on the use of *momordica cochinchinensis* to treat skin disorders are either based on components from inside the seeds or from the root of the *momordica* plant, or a mixture of many different plants, and for very specific skin conditions. None of the invention described below use of the oil in the aril of the plant. Oil of the seeds of "gac" has distinctive compositions and functions, than the oil extracted from the pulp (aril) of the "gac". The patents related to seed oil of "gac" are listed below:

Patent CN101697993(A) filed Apr. 28, 2010 by Fujun et al.

Patent CN101219173 (A); CN1101219173 (B) filed Jul. 16, 2008 by HAIJIANG XIA [CN] described a mixture of Chinese ephedra, radix sileris, cortex lyeii radicis, dictamni cortex and *momordica cochinchinensis* seed to treat psoriasis.

Patent JP2010001264 (A) filed in Jan. 7, 2010 by Takano Kenichai, Kurachi Michio and Noguchi Yuki titled "nerve stretch-inhibiting agent" described the use of *Helicteres isora, Geranium thunbergii, Alpinia galanga, Acanthopanax giraldii, Evodiae Fructus, Salvia splendens, Artemisia apiacea, Melia toosendan, Humullus lupulus, Rubus chingii, Mentha piperita, Monordica cochinchinensis* seed, and *Rosmarinus officinalis* as a preventive or therapeutic agent for itching.

Patent JP2009040691 (A) filed on Feb. 26, 2009 by Takagaki et al. described solutions using *Momordica cochinchinensis* seed coat and extract of seed coat with solvent as skin lighting ingredient. Components in seed coat of *momordica cochinchinensis* are totally different from the aril of the fruit.

Patent JPH09328434 (A) filed Dec. 22, 1997 by Kubo et al. described the use of combination of Jifushi (dried fruit of *Chenopodium scoparia* L.) or Mokubetsukon (dried root of *Momordica cochinchinensis* (Lour.) Spreng.) extracted with alcohol or acetone, or momordin I or momordin IIe which is a saponin component and derived therefrom and expressed by the formula as anti-itch agent.

Plant extracts rich in carotenoids for skin treatment have been proposed before and listed below. None of the compositions listed contained *momordica* oil.

In U.S. Pat. No. 7,618,662 filed in Nov. 17, 2009, Hines, et al, November described compositions include natural plant constituents that stimulate lipid synthesis. The plant extracts are preferably derived from *Rhinacanthus nasutus, Humulus scandens, Sesbania grandiflora, Amorphophallus campanulatu, Pouzolzia pentandra,* and *Piper betel* and any combinations thereof. The compositions are preferably applied to the skin, or are delivered by directed means, to a site in need thereof.

In U.S. Pat. No. 8,007,837 by Mitra et al. filed Aug. 30, 2011, the inventors described a herbal composition for maintaining/caring the skin around the eye. The composition is comprised of extracts of *Saxifraga ligulata* syn. *Bergenia ligulata, Cipadessa baccifera* and *Emblica officinalis*. Other related prior art is provided below:

U.S. Pat. No. 7,592,024 filed Sep. 22, 2009 described Topical compositions containing melicope hayselii and a method of treating skin U.S. Pat. No. 8,329,231 by McNeary et. al, described method of preventing photo aging with ashwagandha and Indian gooseberry;

U.S. Pat. No. 6,800,292 by Murad et al. filed in Oct. 5, 2004 described the use of Pomegranate fruit extract compositions for treating dermatological disorders;

US patent 20040115286 by Lee, Kang-Tae, et. al, filed in Jun. 17, 2004 described cosmetic composition for remedying skin wrinkles comprising bergenia emeiensis extract as active ingredient.

U.S. Pat. No. 7,547,456 by Martin et al, Jun. 16, 2009 described the Composition containing feverfew extract.

U.S. Pat. No. 6,365,630 filed Apr. 2, 2002 by Fisher et al. described compositions and methods ameliorating various effects of UVA and UVB radiation from the sun. The compositions including an ingredient that prevents photoaging from MED and subMED radiation, such as a retinoid, certain other compounds (such as N-acetylcysteine, 2-furildioxime, and vitamin C) and optionally other MMP inhibitors such as tetracyclines and/or compounds that inhibit the P-450-mediated metabolism of retinoids such as ketoconazole and other azole compounds.

A number of workers have prepared formulations of carotenoids for therapeutic use including the work reported in the documents discussed below. None of the inventions below described the use of *momordica* oil for carotenoids, nor a combination of vitamin E as a preservative and an antioxidant to spare carotenoids in the compositions, in combination with essential fatty acids to nourish the skin.

Bos, et al. in U.S. Pat. No. 8,197,851 filed Jun. 12, 2012 described a method to produce a carotenoid composition comprising the carotenoid as particles of size smaller than 100 nanometers in an oil medium.

U.S. Pat. No. 5,460,823 (Jansen et al) relates to a process of preparing microparticles of carotenoids in which solids are milled in an aqueous medium in the presence of a hydrocolloid. The mixture is spray dried to for microparticles of maximum particle size of about 10 microns.

U.S. Pat. No. 5,811,609 (Vilstrup et al) likewise prepares particles by milling carotenoids in aqueous medium to form a suspension in the presence of a hydrocolloid. The suspension is heated to cause melting of the carotenoid which is spray dried to form a powder, U.S. Pat. No. 6,639,113 (Runge et al) describes the preparation of powdered oxygenated carotenoids such as astascanthin which are formed by dissolving the composition of the oxygenated carotenoid in a solvent at 50.degree. C. to 240.degree, C. which is mixed with a protecting colloid and set before conversion to a powder by spray drying or the like methods. Chimia 21, 329 (1967), (see also DE Application No. 12 11 911 and DE Publication No. 25 34 091 disclose methods of dissolving the active compound in a chlorinated organic solvent, emulsifying the solution in a gelatine/sucrose solution and extracting the solvent from the emulsion causing the active compound to crystallize in microcrystalline form. A disadvantage of this method is that it is technically impossible to remove the organic solvent completely and the solvent is a potential hazard during the process and as residues in the final product.

U.S. Pat. No. 5,827,539 (Gellenback at al) prepares a dry carotenoid powder by grinding in an oil to provide particles of about 0.5 microns which are dispersed in an aqueous encapsulating media. Emulsification and drying need to be controlled to avoid the formation of sticky agglomerates of poor stability, U.S. Pat. No. 6,132,790 (Schlipalius) describes a carotenoid in an oil solvent which is dispersed in an aqueous phase in the presence of an emulsifier to provide fine droplets of oil phase.

U.S. Pat. No. 5,773,026 (Schlipalius) describes use of a natural carotenoids oil composition in a non-toxic water dispersible therapeutic formulation suitable for injection or intravenous use by humans or animals.

U.S. Pat. No. 6,428,816 (Schlipalius et al) describes treatment of melanoma or melanomas by injection of a water insoluble carotenoid component and a mixture of a water dispersible component.

U.S. Pat. No. 5,780,056 (Akamatsu et al) describes natural carotenoid formulated as capsules having a multi core structure provided by heating the carotenoid to 120 degree. C. in an oil and cooling to 70.degree. C. before forming a water in oil emulsion and inverting the phases and encapsulating the resulting oil-in-water emulsion as microfine oil particles.

Methods for manufacturing an enhanced cosmetic skin care toner are described in a 2006 U.S. Pat. No. 7,122,211 (Jensen, et al). The invention advances prior art toners by providing a toner formulated with *Morinda Citrifolia*, or *Noni*, from the Indian Mulberry plant. The addition of *Noni* to the toner of the present invention serves to provide significant skin care advantages not found in prior art toners.

Composition and method of preparing a tomato-based topical formulation for enhanced healing of burns, ultraviolet and radiation erythema is described in U.S. Pat. No. 8,318,215 by Ryngler-Lewnsztain, et. al, (2012)

Compositions and methods for improving the health and appearance of skin using novel decolorized microalgae were provided by Avila, et al, in U.S. Pat. No. 8,298,548 (2012) in which the inventors also described using polysaccharides for topical personal care products, cosmetics, and wrinkle reduction Dryer et. al, (U.S. Pat. No. 8,304,455, 2002) described improvements to the aesthetic appearance of skin, using topically applied active agents which increase expression levels of genes associated with the dermatological signs of aging.

In U.S. Pat. No. 8,216,619 Giori, et al. (2012) described the use of carotenoid isomers for skin and hair by manufacturing a stable composition enriched in cis-lycopene (z-isomers), achieved through prolonged heating in solvents of tomatoes, parts of tomatoes, derivatives thereof, or tomato extracts in solvents.

Stutz, et al. (2012, U.S. Pat. No. 8,206,721) used an extract from snow algae, *Chlamydocapsa* sp as an anti-aging and environmental protection agent in cosmetic and/or pharmaceutical products. This patent claims to guard U.S. Pat. No. 8,277,849 Dillon, et al. Oct. 2, 2012 describes microalgae-derived compositions for improving the health and appearance of skin. Provided herein are microalgal skin care compositions and methods of improving the health and appearance of skin. Also provided are methods of using polysaccharides for applications such as topical personal care products, cosmetics, and wrinkle reduction compositions. The invention also provides novel decolorized microalgal compositions useful for improving the health and appearance of skin. The invention also includes insoluble polysaccharide particles for application to human skin.

In U.S. Pat. No. 8,221,766, Dryer et. al (2012) describes the Use of plant extracts derived from *Populus nigra, Rhinacanthus nasutus, Sapindus rarak*, and *Thumbergia laurifolia*, and any combinations thereof, wherein the compositions include natural plant constituents that inhibit at least one cytokine, to prevent and/or reduce the signs of subjective discomfort and/or irritation in the topical application of cosmetic products.

Essential fatty acids (EFAs) including omega-3, omega-6, omega-9 have been shown to exert therapeutic benefits to skin. The use of fatty acids in skin care formulation has been described by other workers and listed in the references section. Various plant materials, and synthetic compounds were used, however, none of the inventions describes the use of *momordica* oil as the main component providing EFAs. The subsequence paragraph lists some patents related to the use of essential fatty acids, or omega-3 in cosmetic or skin care formulations.

Morariu, in U.S. Pat. No. 7,776,915 (2010) provided a topical composition useful in improving the appearance of aged skin characterized by wrinkles and loss of elasticity. The invention was comprised of a lipoic acid, a carnitine, and a carnosine in a suitable vehicle for topical application. The present compositions are Preferred components include R-lipoic acid or R-dihydrolipoic acid, acetyl-1-carnitine, and 1-carnosine, The use of Cosmetic oil substances is described in Ausmann et al, U.S. Pat. No. 8,148,561 (2012) in which a storage-stable, smooth-feeling, non-comedogenic fatty acid ester mixture of 2-ethylhexanol and fatty acids comprising 2-ethylhexyl fatty acid esters, wherein the aggregate amount of $C_{12}$ and $C_{14}$ 2-ethylhexyl fatty acid esters is 85% or more of the mixture, based on the total weight of all fatty acid esters in the mixture, which mixtures are useful in or as an oil component of a cosmetic or pharmaceutical preparation.

U.S. Pat. No. 7,780,873 by More-Gutierrez, et al filed in Aug. 24, 2010 described a bioactive complex composition having enhanced oxidative stability, emulsion stability mineral rich transparent beverages and a wide range of functional health benefits. The composition may include as a base composition individual ingredients or a synergistic blend of mineral salts, Omega-3 rich oils, phospholipids, chitosan, and alpha-casein, beta-casein, kappa-casein or protein fragments, glycopeptides, phosphopeptides. The composition may optionally be further utilized for the prevention of hypercholesterolemia, bone (and teeth) mineral loss, treatment of mental health diseases, heart health, additional nutritional supplementation, and treatment of additional medical conditions.

U.S. Pat. No. 7,531,196 by Kopas, et al, May 12, 2009 described a cosmeceutical formulation that includes a mixture of a refined, bleached, deodorized (RBD) palm oils and red palm olein. The resulting formulation is a homogeneous blend with a considerable shelf life. The formulation may be a cream, lotion, sunscreen, or a soap and may be formulated to include additional beneficial oils and EFAs.

In view of the forgoing, formulations containing carotenoids, vitamin E in *momordica* oil rich in essential fatty acids to protect and nourish skin are proposed.

6. DETAILED DESCRIPTION OF INVENTION

The present invention relates to formulations containing carotenoids, vitamin E, vitamin A in an oil containing essential fatty acids (EFA), to be used for skin protecting and nourishing against oxidative and sun damage.

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting.

DEFINITION OF TERMS

In describing and claiming the present invention, the following terminology will be used.

The singular forms "a," "an," and "the" include plural referents unless the context clearly dictates otherwise. Thus, for example, reference to "a carrier" includes reference to one or more of such carriers, and reference to "an excipient" includes reference to one or more of such excipients.

As used herein, "formulation" and "composition" may be used interchangeably herein, and refer to a combination of two or more elements, or substances. In some embodiments a composition may include an active agent and a carrier.

As used herein, "effective amount" or "antioxidant absorption enhancing amount" refers to an amount of an ingredient, namely composition, is sufficient to achieve an intended compositional or physiological effect. Thus, a "therapeutically effective amount" refers to a non-toxic, but sufficient amount of an agent, including active agents, to achieve therapeutic results in preventing or ameliorating a condition for which the active agent is known to be effective, or in attaining a desired physiologic effect. It is understood that various biological factors may affect the ability of a substance to perform its intended task. Therefore, an "effective amount," "antioxidant absorption enhancing amount," or a "therapeutically effective amount" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986), incorporated herein by reference.

As used herein, "carrier" or "inert carrier" refers to a substance with which a bioactive agent or a nutritional agent may be combined to achieve a specific dosage formulation for delivery to a subject. As a general principle, carriers must not react with the bioactive agent in a manner which substantially degrades or otherwise adversely affects the bioactive agent or its potency.

As used herein, "excipient" refers to substantially inert substance which may be combined with an active agent and a carrier to achieve a specific dosage formulation for delivery to a subject, or to provide a dosage form with specific performance properties. For example, excipients may include but are not limited to binders, lubricants, etc., but specifically exclude active agents and carriers.

As used herein, "subject" refers to a mammal that may benefit from the administration of a composition or method as recited herein. In this document, the subject will be a human.

As used herein, "administration," and "administering" refer to the manner in which an active agent, or composition containing such, is presented to a subject. Administration can be accomplished by various routes well-known in the art including topical or oral methods.

As used herein, "coadministration" refers to administration of two or more active agents in a manner that will allow them to be present together in-vivo for period of time. Accordingly, while the term "coadministration" includes simultaneous administration of two or more active agents, and administration from a single formulation, it is to be understood that it is not limited thereto.

"Topical administration" can be achieved by applying on skin, on hand, body, face, cuticle or lip. Examples of well known topical dosage forms include gel, oil, cream, beauty bar, lotion, etc.

"Oral administration" can be achieved by swallowing, chewing, or sucking of an oral dosage form comprising the drug. Examples of well known oral dosage forms include tablets, capsules, caplets, powders, granulates, beverages, syrups, elixirs, confections, or other food items, etc.

As used herein, "extract" when used in connection with a plant, tree, herbs, fungus, etc., refers to material which has been removed from the source, or a portion thereof, including the flower, fruit, seed, peel, leaf, root, bark, stem, etc. As will be recognized by those of ordinary skill in the art, extracts may be either crude or refined to a selected degree in order to isolate specified materials or active agents. Extracts can take a variety of forms including powders, juices, purees, etc. A number of extraction processes that can be employed to produce the compositions of various types will be recognized by those skilled in the art, such as dehydration, lyophilization, etc.

"Synergistic", "synergism", "synergistically effective" or "synergistically enhances", may be used interchangeably and refer to a situation in which the combined effect of two agents is greater than which would be predicted from their individual effects. Various mechanisms for calculating or otherwise determining synergism are known to those of ordinary skill in the art.

"Antioxidant" refers to a chemical compound, an enzyme or other organic molecule which prevents free radicals from causing oxidation of molecules in the body. Susceptible molecules include without limitation, such vital entities as DNA, RNA, lipids (fats), and proteins. The antioxidant, by reacting with the oxidant, protects these important molecules from being damaged. Examples of antioxidants include without limitation, vitamins A, C, E, carotenoids, polyphenols, and certain minerals.

The term "Gac oil", "*momordica* oil", "redmelon oil", "gac oil extract" refer to an oil extract from the seed pulp from the fruit of the plant *Momordica cochinchinensis* Spreng, or of plants significantly related thereto, grown anywhere in the world including blends, mixtures, and combinations of such strains and relatives.

As used herein, the terms "bioavailable" or "bioavailability" when used in connection with antioxidants refer to the antioxidant portion of a formulation which is available to be absorbed or taken up by the target tissue, in this application skin.

As used herein the term "stability" when used in connection with carotenoids refer to the portion of the carotenoids in the formulations that is not destroyed or oxidized or loss and available for the uptake into the applied area of the skin.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.5 to 400 should be interpreted to include not only the explicitly recited concentration limits of 0.5 and 400, but also to include individual concentrations within that range, such as 0.5, 0.7, 1.0, 5.2, 8.4, 11.6, 14.2, 100, 200, 300, and sub-ranges such as 0.5-2.5, 4.8-7.2, 6-14.9, 55, 85, 100-200, 117, 175, 200-300, 225, 250, breadth of the range or the characteristic being described.

7. BRIEF DESCRIPTIONS OF DRAWINGS

Figure 1B:
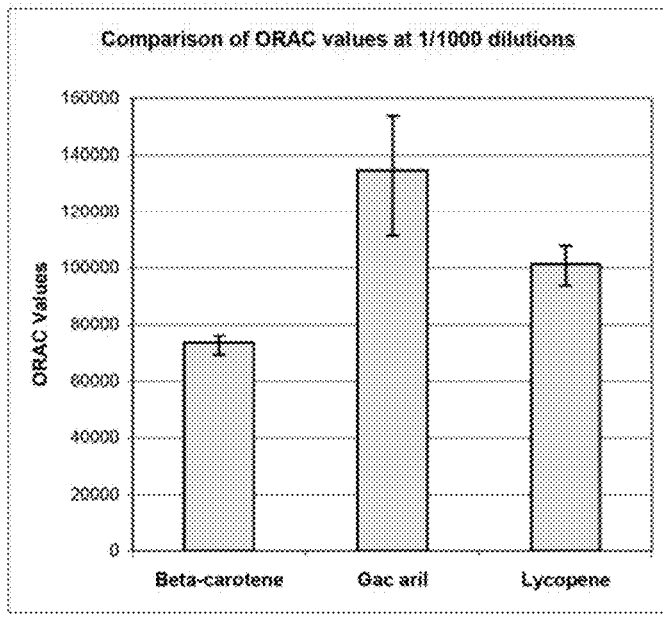

FIG. 1a and FIG. 1b

Those figures depict graphical comparison of the antioxidant values of *momordica cochichinchinensis* (gac) aril, β-carotene, and lycopene using Radical Antioxidant Capacity (ORAC) assay, ORAC values were obtained using a Trolox standard linear regression line. FIG. 1a shows the antioxidant capacity of the antioxidant samples in 1/100 dilution of the stock solutions. FIG. 1b shows the values in 1/1000 dilution of the stock solutions of each antioxidant sample.

8. DETAILED DESCRIPTION OF THE INVENTION

The present invention encompasses methods and safe formulations of carotenoids, well established skin protection compounds, vitamin E, and essential fatty acids to protect and moisturize skin. In one aspect the formulation includes the oil extract from "gac" fruit in combination with other fruit oil. Gac fruit oil is oil extracted from the aril (seed pulp) of *momordica cochinchinensis*. In this invention gac oil or redmelon oil is obtained by cold press technique, and not from chemical solvents. One method for extracting Gac oil as described in U.S. Pat. No. 6,770,585 which is incorporated herein by reference.

The oil contains between 5000 to 6000 μg/1 mL of carotenoids the main bioactive components are beta-carotene and lycopene. The oil also contains alpha-tocopherol which functions as a natural preservative, spares the carotenoids and fatty acids from being oxidized (long shelf-life). In addition, the fatty acid profile of "gac" oil is balance in mono-unsaturated and poly-unsaturated rendering it stable at room temperature. The oil contains at least 32% of poly-unsaturated and 34% of mono-unsaturated. Among the PUFA, 31% is linoleic, and 1% is eicosanoic, and 0.1% is arachidonic. Other EFA are docosanoic and tetracosanoic. Total essential fatty acids is 33.5%.

In one embodiment, avocado oil is added to change the oleic fatty acid (47.20%), followed by palmitic (23.66%), linoleic (13.46%) docosadienoic (8.88%), palmitoleic (3.58%), linolenic (1.60%), eicosenoic (1.29%), and myristic acids (0.33%). In other embodiments, grapeseed oil is added to increase alpha-tocopherol level. In other embodiment olive oil is added, which enhance polyphenol level, and mono-unsaturated fatty acids. Solidity or viscosity of the formulation can be changed if a solid form is desired by adding into the formulation coconut oil. In one embodiment, cold press coconut oil was added.

The naturally occurring antioxidants found in gac oil have been shown to scavenge free radicals and in return improve the regeneration effects of the body's immune system. In addition it has been suggested that the affects of gac oil increase the levels of important bodily antioxidant enzymes such as superoxide dismutase (SOD) and glutathione peroxidase (GSHPx) and as a result reduce the affects of aging on the skin, increases vision and protection against cancer.

As noted above, antioxidants are one of the many protective compounds found in the body and plants. The main function of antioxidants is to neutralize free radicals in cells. It has been suggested that free radicals cause premature aging, and cancer. Free radicals are highly reactive byproducts of chemical processes. Free radicals produce harmful oxidation reactions which damage the integrity of cells and body tissues. For these reasons skin care formulation containing antioxidants have become popular in recent years.

It has now been recognized that antioxidants including vitamin A promote strong and healthy immune system, aid in the development of new cells, help maintain cell membrane integrity and reduce keratin formation caused by aging. Further, antioxidants have special properties that neutralize free radicals. In many cases, a distinctive pattern of alternating single and double bonds found in the antioxidant compounds provides the functionality allowing the compound to absorb excess energy from free radical compounds. Certain antioxidant compounds have higher potencies and have slightly different functions. For example, carotenoids and flavonoids appear to be some of the most potent antioxidants. In addition, different plants supply higher concentrations and potencies of antioxidant compounds.

As will be recognized by those of ordinary skill in the art, antioxidants sources are abundant in nature and can be derived or extracted from many different species of plants. Specific examples of antioxidant compounds that can be utilized in the present invention include without limitation, carotenoids, polyphenols, and tocopherols. In one embodiment the antioxidant compound selected can be beta-carotene. In another aspect of the present invention the antioxidant compound can be lycopene.

Since vitamin A in the formula comes from beta-carotene, the use of the formulation on skin does not have toxicity as the use of synthetic retinol or retinoic acid. In one embodiment, the subject applied 1 oz skin oil which provided a safe precursor form of retinol in another embodiment, a subject applied 1 mL of skin cream around dry areas of skin on hand.

The formulation provided 2710 μg retinol in a safe carotenoid form 334 μg alpha-tocopherol, 3020 μg of lycopene and 50 mg of essential fatty acids. The formulation of the present invention can provide for increases of antioxidants and moisturizing to the skin after continuous application. In one embodiment skin softness and improvement of a subjects after applications of the skin oil for two days described herein could be seen. The improvement in skin dryness due to absorption of antioxidants and EFAs as compared to an equivalent total antioxidant application that does not include Gac oil.

The skin care formulations of the present invention can be present in a single composition or in a combination of multiple formulated skin nutrition compositions which are co-administered to a subject. In one embodiment, the topical skin nourishing formulation is a single formulation containing an effective amount of Gac oil and at least one other fruit or vegetable oil.

The nourishing skin formulations include can include Gac oil and at least one other antioxidant and EFA rich oil.

The at least one plant oil rich in essential fatty acids and antioxidants other than carotenoids can include, but is not limited to avocado oil, coconut oil, olive oil, safflower oil, rosehip seed oil, apricot kernel oil (carrier oil). Other plant oil such as peppermint oil, lavender oil, rosemary oil have been shown to exert analgesic, antibacterial, anti-inflammatory, antifungal, antimicrobial, antiseptic properties. Composition of the plant oil may be pH—4.16; Fatty Acids profile contains Oleic-68.9%; Palmitic-4.9%; Linoleic-22.4%; Stearic-1.2%.

In one embodiment, the at least one plant extract can include or consist of safflower and lavender oil. In another embodiment, the at least one plant extract can include or consist of avocado oil and coconut oil. In yet another embodiment, the at least one oil extract can include or consist of coconut and grapeseed oil. In still another embodiment, the at least one oil can include or consist of olive extract, apricot seed oil and rosehip seed oil.

The Gac component of the present formulation is included in an oil form, without applying any high heat to protect carotenoids and other bioactive compounds. Gac fruit oil may be obtained by any process of processing, separation or active ingredient extraction known to those skilled in the art. By way of example, without limitation, extraction techniques, such as cold press, expeller pressed, supercritical fluid extraction, centrifuge, distillation or co-pressing. Other carrier oil used in the formulation might be partially refined or unrefined.

In accordance with the present invention, the amount of Gac extract contained in the skin nourishing formulation may be varied according the knowledge of one skilled in the art in order to achieve a particularly desired result. However, the Gac oil content may be from about 0.1% wt % to about 20 wt % of the formulation. In one aspect, the amount may be from about 3.0 wt % to about 15 wt % of the formulation. In another aspect, the amount may be from about 4.0 wt % to about 9.0 wt % of the formulation.

Coconut oil is also known as *Cocos nucifera* acts as a barrier agent for skin. Coconut oil is solid at room temperature, and is used as a carrier also as a solidifier. When coconut oil is present in the skin nourishing formulations of the present invention it can comprise from about 0.1 wt % to about 35 wt % of the formulation. In one aspect, the amount may be from about 0.5 wt % to about 10 wt % of the formulation.

Olive extract and olive oil when incorporated in the skin nourishing formulation, can also enhance anti-inflammatory effect, which has been published. Olive oil is high in polyphenols, vitamin E and vitamin C. According to one aspect of the present invention, the amount of olive oil contained in the skin nourishing formulation may be varied depending on the amount of other extracts present and the desired result. When olive oil is included in the skin nourishing formulation it can comprise from about 2 wt % to about 20 wt % of the nutritional composition. In yet another aspect, the amount may be about 1.0 wt % to about 5.0 wt % of the skin nourishing composition.

Safflower oil is also known as *Carthamus tinctorius* contains high concentration of oleic acid and has been used as a moisturizing oil. The amount of safflower oil contained in the skin nourishing formulation may be varied depending on the amount of other extracts present and the desired result. When Safflower oil is present in the skin nourishing formulations of the present invention it can comprise from about 0.1 wt % to about 30.0 wt % of the formulation. In one aspect, the amount may be from about 0.5 wt % to about 10 wt % of the formulation.

Almond oil is also known as *Prunus dulcis*, is extracted from raw almond kernels by expeller press. Almond oil is an emollient and has been known to soften, soothe, and recondition the skin. Almond oil is used as a carrier oil and an addition to body care formulation. from raw almond kernels and exceptionally rich in essential fatty acids, and vitamin E. When almond oil is present in the skin nourishing formulations of the present invention it can comprise from about 0.1 wt % to about 20.0 wt % of the formulation. In one aspect, the amount may be from about 0.5 wt % to about 10 wt % of the formulation. In one aspect, the amount of almond oil may be about 4.0 wt % to about 9.0 wt % of the formulation.

Sunflower oil is also known as *Helianthus annuus*. The oil contains high level of oleic acids, vitamin D and E, and lecithin. Sunflower oil is high in unsaturated fatty acids, and has been shown to be able to deeply penetrate and recondition skin. It has been used to treat dry, weathered, aged, and damaged skin.

Rosehip seed oil is also known as *Rosa rubiginosa*. The oil is extracted by cold press from the ripened fruit of Rosehip, also known as *Rosa Mosqueta*. The oil is high in essential fatty acids and has been known as a great agent in the fight against dry, weathered, and dehydrated skin. It works wonders on scars and is the predominant oil used for treating wrinkles and premature aging. When rosehip oil is present in the skin nourishing formulations of the present invention it can comprise from about 0.1 wt % to about 2.0 wt % of the formulation. In one aspect, the amount may be from about 0.5 wt % to about 5 wt % of the formulation Examples additional oil which can be included in the skin nourishing formulations include but are not limited to mint essential oil, lavender oil, rosemary oil, mandarin orange oil, orange peels, and orange oil, and combinations thereof. When present in the skin nourishing formulations, the oil(s) can comprise from about 0.1 wt % to about 10 wt % of the skin nourishing formulation.

Other skin health imparting substances which may be combined with the desired Gac oil in the formulation of the present invention include raw honey and wax to achieve the desire affects.

Other nutritious addition might be amino acids, ionic minerals, and naturally occurring anti-oxidants. Excipients may also be present in the skin nourishing formulations of the present invention. Excipients can include stabilizers, preservatives, flavoring agents, thickeners, etc. Non-limiting examples of excipients include wax, honey, coco butter, natural essential oil, and fragrances. The excipients can be present individually or in combinations. It is important that the excipients do not alter or inhibit the antioxidant potency of the skin nourishing formulations.

The skin nourishing formulations of the present invention can also include a small amount of water. Water can comprise from about 0.1 wt % to about 5 wt % of the skin nourishing formulation.

The amount of carotenoid compounds obtained from the fruit extracts may vary from fruit to fruit. Typically, the carotenoid family is responsible for most of the pigments found in plants. For example, carotenoids produce the orange pigments found in pumpkins and carrots, and red pigments in tomatoes. In addition to the color imparting properties, carotenoids as a whole are highly effective at quenching singlet oxygen (an unstable and highly reactive oxygen compound) and are a direct scavenger of free radicals. Carotenoids are defined by their chemical structure. The majority of carotenoids are derived from a 40-carbon polyene chain. The distinctive pattern of alternating single and double bonds in the polyene chain provides the functionality allowing carotenoids to absorb (quench) excess energy from singlet oxygen compounds. Some specific examples of carotenoids are alpha-carotene, beta-carotene, lycopene, astaxanthin, lutein, and zeaxanthin. Lycopene and beta-carotene may be the most effective of the carotenoids at quenching singlet oxygen.

Other antioxidants may have singlet oxygen quenching potential such as, alpha-tocopherol, alpha lipoic acid, flavonoids, etc. Singlet oxygen quencher compounds should have electron-rich structures such as double bonds in the molecules to react with and stabilize singlet oxygen reactions. Flavonoids for example, have been suggested to act as scavengers of various oxidizing species. Flavonoids stem from polyphenol compounds. Generally phenolic compounds, and in most flavonoids and flavonoids, contain groups capable of quenching radicals. The phenolic group is responsible for stabilizing and quenching the unstabilized energy of a free-radical. A high percentage of flavonoids are found mainly in citrus plants, grapes and berries.

In another aspect, the present invention relates to a method of providing a skin nourishing formulation comprising the active ingredients of an extract from Gac oil in combination with at least one other antioxidant and EFA source. The formulation of the present invention provides for enhanced carotenoid antioxidants and vitamin A, stability and bioavailability in the formulation as compared to an antioxidant formulations.

In yet another aspect of the present invention, a skin nourishing formulation providing even further enhancement of antioxidant bioavailability is provided. The formation provides Gac oil extract, at least one other antioxidant, and at least one other lipophylic antioxidant and skin moisturizing agent, such as vitamin E (alpha-tocopherol), is provided. Alpha-tocopherol serves as a natural preservative for the lipid formulation. The natural plant source of vitamin E is in palm oil, rice bran oil, coconut oil. Vitamin E has been well studied and its skin therapeutic benefit has been demonstrated. Vitamin E in the oil composition in this invention also spare the carotenoids and rendering the carotenoids more stable and thus bioavailable for absorption.

Generally, the skin nourishing formulation may be provided as a topical form. However, in one aspect of the present invention the skin nourishing formulation may be a variety of oral dosage forms are well known to those of ordinary skill in the art, and specific formulation ingredients may be selected in order to provide a specific result.

Typically, the skin nourishing formulation is formulated in a oil blend, liquid or semi-solid form. Other topical dosage forms may also be implemented with the present formulation. For example, and without limitation, cream, gel, solid bar, or foam or (lip)balm. Accordingly, in one aspect of the present invention, the composition may be a dosage form selected from the group consisting of skin oil, body oil, skin cream, clay, salt, skin mask, butter, cuticle cream, where the skin nourishing formulation utilizes other ingredients, such as aromatic oil, honey, wax gel, scrubbing or skin bleaching causing ingredients.

A study was carried out to demonstrate the antioxidant capability of the major carotenoids β-carotene and lycopene, and of gac aril using the Total Oxygen radical Scavenging Capacity (TOSC) and Oxygen Radical Absorbance capacity (ORAC) assays following published method (A R Garrett, 2010, ST Senthilmohan 2009). Antioxidant capacities were assessed by the overall abilities of the compounds to suppress peroxyl radicals generated from the thermal homolysis of 2,2'-azobis-amidinopropane. Stock solutions of all samples were diluted 1/100 and 1/1000. At a 1/100 dilution, lycopene exhibited the highest ability to scavenge peroxyl radicals, 2.4 and 1.4 times as much as β-carotene and the Redmelon™ aril, respectively (FIG. 1a). However, at a lower concentration (dilution of 1/1000), the gac aril provided the highest peroxyl radical-scavenging capacity, 1.8 and 1.3 times as much as β-carotene and lycopene, respectively (FIG. 1b).

Using the TOSC method, it was apparent that total antioxidant activities of beta-carotene and lycopene in *momordica cochinchinensis* aril were high (2 times higher than Trolox), an analogue of Vitamin E commonly used a gold standard. The comparative TOSC values (cTOSC) of gac (Redmelon™) aril maintains 5.4 times greater than Trolox. Lycopene was the most active, maintaining a peroxyl radical scavenging capacity (rTOSC) 24 times greater than Trolox. The results are summarized below in the following table

| Sample | cTOSC | rTOSC |
|---|---|---|
| Trolox | 1.00 | 4.51 |
| Gac Aril | 5.44 | 24.55 |

In summary, beta-carotene and lycopene in the gac oil demonstrated higher concentration and antioxidant capacity (50% higher than Trolox). Also demonstrated that antioxidant capacity of gac oil is higher than pure beta-carotene and lycopene at higher dilution level.

It is to be understood that the above-described arrangements are only illustrative of the application of the principles of the present invention. Numerous modifications and alternative arrangements may be devised by those skilled in the art without departing from the spirit and scope of the present invention. Thus, while the present invention has been fully described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

The scope of the invention is, therefore, indicated by the appended claims rather than by the forgoing description.

EXAMPLES

The following examples are given to illustrate various embodiments which have been made or may be made in accordance with the present invention. These examples are given by way of examples only, and it is to be understood that the following examples are not comprehensive or exhaustive of the many types of embodiments of the present invention which can be prepared in accordance with the present invention Example 1

A nourishing and protecting lip balm composition consists redmelon oil, coconut oil, a stabilizer such as wax, and natural flavoring substance such as honey, mandarin orange, vanilla, mint, olive oil, avocado oil.

Example 2

A skin nourishing and protecting oil consisting of redmelon oil, olive oil, avocado oil, and natural flagrance such as vanilla, orange.

Example 3

A skin nourishing and protecting bar consisting of redmelon oil, coconut oil, a stabilizer such as wax, and natural flavoring such as lavender oil, orange oil

Example 4

A skin nourishing and scrubbing composition consisting of redmelon oil, scrubbing ingredients such as orange peels, oat meal, rice bran.

Example 5

A skin protecting and nourishing cream composition consisting of redmelon oil, olive extract, apricot kennel oil, and rosehip oil.

It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, lotion, food or bar manufacturing process as well as vitamins, herbs, flavorings and carriers. Other such changes or modifications would include the use of other herbs or botanical products containing the combinations of the preferred embodiments disclosed above. Many additional modifications and variations of the embodiments described herein may be made without departing from the scope, as is apparent to those skilled in the art. The specific embodiments described herein are offered by way of example only.

9. REFERENCES

U.S. Pat. Documents

| | | |
|---|---|---|
| 6,770,585 | Vuong | Feb. 5, 2004 |
| 8,007,837 | Mitra, et al. | Aug. 30, 2011 |
| 6,235,721 | Ghosal | May 22, 2001 |
| 8,197,851 | Bos, et al. | Jun. 12, 2012 |
| 7,435,846 | Olvera, et al. | Oct. 14, 2008 |
| 7,141,712 | Choo | Nov. 28, 2006 |
| 8,329,231 | McNeary et, al | Dec. 11, 2012 |
| 6,682,763 | Kuno, et al. | Jan. 27, 2004 |
| 20040115786 | Lee, Kang-Tae, et. al, | Jun. 17, 2004 |
| 7,572,468 | Ishida, et. al, | Aug. 11, 2009 |
| 6,800,292 | Murad | Oct. 5, 2004 |
| 8,318,220 | Koganov | Nov. 27, 2012 |
| 7,122,211 | Jensen, et al. | Oct. 17, 2006 |
| 8,318,215 | Ryngler-Lewensztain, | Nov. 27, 2012 |
| 8,298,548 | Avila, et al. | Oct. 30, 2012 |
| 8,206,721 | Stutz, et al. | Jun. 26, 2012 |
| 8,277,849 | Dillon, et al. | Oct. 2, 2012 |
| 8,221,746 | Isaacs, et al. | Jul. 17, 2012 |
| 6,365,630 | Fisher, et al, | Apr. 2, 2002 |
| 8,304,455 | Dryer et al. | Nov. 6, 2002 |
| 8,216,619 | Giori, et al. | Jul. 10, 2012 |
| 7,557,146 | Sabio Rey | Jul. 7, 2009 |
| 8,067,045 | Smidt, et. al. | Nov. 29, 2011 |
| 20090110789 | Mower et al | Apr. 30, 2009 |
| 7,618,662 | Hines, et al | Nov. 17, 2009 |
| 7,592,024 | Ptchelintsev, et al | Sep. 22, 2009 |
| 7,547,456 | Martin et al | Jun. 16, 2009 |
| 5,460,823 | Jansen et al | Oct. 24, 1995 |
| 5,811,609 | Vilstrup et al | Sep. 22, 1998 |
| 6,639,113 | Runge et al | Oct. 28, 2003 |
| 5,827,539 | Gellenback at al | Oct. 27, 1998 |
| 6,132,790 | Schlipalius | Oct. 17, 2000 |

U.S. Pat. Documents -continued

| | | |
|---|---|---|
| 5,773,026 | Schlipalius | Jun. 30, 1998 |
| 6,428,816 | Schlipalius et al | Aug. 6, 2002 |
| 5,780,056 | Akamatsu et al | Jul. 4, 1998 |
| 8,221,766 | Dryer et al | Jul. 17, 2012 |
| 7,776,915 | Morariu | Aug. 17, 2010 |
| 8,148,561 | Ansmann et al | Apr. 3, 2012 |
| 7,780,873 | More-Gutierrez, et al | Aug. 24, 2010 |
| 7,531,196 | Kopas et al | May 12, 2009 |
| 5,942,233 | Chang, Teh Shan | Aug. 24, 1999 |
| U.S. Pat. No. 4,997,649 | Papaconstantin et al. | Mar. 5, 1991 |
| CA1275249 | Horrobin | Oct. 16, 1990 |
| 2004219239 | Castelli, et al. | Nov. 4, 2004 |
| 2012034320 | Murray, et al. | Feb. 9, 2012 |
| 2009047378 | Stewart, et al. | Feb. 2, 2009 |
| 2008286390 | Tanyi | Nov. 20, 2008 |
| 2007015438 | Lange, et al. | Jan. 18, 2007 |
| 2006257352 | Saar, et al. | Nov. 16, 2006 |
| 2011014141 ( | Nakayama, et al. | Jan. 20, 2011 |

Foreign Pat. Documents

| | | |
|---|---|---|
| CN101697993 (A) | Fujun et al. | Apr. 28, 2010 |
| CN101219173 (A); | Haijian Xia | Jul. 16, 2008 |
| JP2010001264 (A) | Takano Kenichi, et al. | Jan. 7, 2010 |
| JP2009040691 (A) | Takagaki et al. | Feb. 26, 2009 |
| JPH09328434 (A) | Kubo et al. | Dec. 22, 1997 |
| CN102552758 (A) | Chunrong Yu, et al. | Jul. 11, 2012 |
| KR20110063362 (A) | Lee Hyun Woo | Jun. 10, 2011 |
| CN102462816 (A) | Qiuen Zeng | May 23, 2012 |
| CN101697993 (A) | Fujun Sum, et al. | Apr. 28, 2010 |
| JP2011020947 (A) | Son Manchu | Feb. 3, 2011 |
| CN101549137 (A) | Shaobin Yu, et al. | Oct. 7, 2009 |
| JP2010174825 (A) | Isobe Masaichi | Jun. 10, 2010 |
| CN101401922 (A) | Guozhong Zhang | Apr. 28, 2009 |
| CN101254232 (A) | Bianzong, Xie | Sep. 3, 2008 |
| JP2009178079 (A) | Horie Sachiyo, et al. | Aug. 13, 2009 |
| CN101214361 (A) | Wenhao, Li | Jul. 9, 2008 |
| CN102305838 (A) | Lijia Fu, et al. | Jan. 4, 2012 |
| CN101485817 (A) | Lijia Fu, et al. | Jul. 22, 2009 |
| CN101152571 (A); | Songhua Hu, et al. | Apr. 2, 2008 |
| CN101156901 (A); | Zongxiang He et al. | Apr. 9, 2008 |
| CN101219173 (A); | Haijiang Xia | Jul. 16, 2008 |
| RU2008129710 (A); | Kim Bong Cheol, et al. | Jan. 27, 2010 |
| JPH1149692 (A) | Yamahara Joji | Feb. 23, 1999 |
| JPH1112178 (A) | Kubo Michitoku, et al. | Jan. 19, 1999 |
| MY125557 (A) | Shan Chang Teh | Aug. 30, 2006 |
| JPH09328434 (A) | Kubo Michitoku, et al | Dec. 22, 1997 |
| JPH1059858 (A) | Yamahara Joji | Mar. 3, 1998 |
| KR20100056168 (A) | Park, et al. | May 27, 2010 |
| KR20090085844 (A) | Woo, et al. | Aug. 10, 2009 |
| KR20080038812 (A) | Kyoung, et al. | May 7, 2008 |
| KR100757043 (B1) | Hee, et al. | Sep. 7, 2007 |
| KR20050026889 (A) | Iotsove, et al. | Mar. 16, 2005 |
| DE10340684 (A1) | Holtkoetter, et al. | Jul. 22, 2004 |
| JP2006169111 (A) | Takashi, et al. | Jun. 29, 2006 |
| CA2281425 (A1) | Gerd, et al. | Mar. 4, 2000 |
| MX9806169 (A) | Chambers, et al. | Oct. 13, 1998 |
| JPH115727 (A) | Yasutomo, et al. | Jan. 12, 1999 |
| JPH092939 (A) | Yasuhiko, et al. | Jan. 7, 1997 |
| WO2013043028 (A1) | Voicehovska | Mar. 28, 2013 |
| WO2012109152 (A1) | Banov, et al, | Aug. 16, 2012 |
| WO2011130788 (A1) | Skilton | Oct. 27, 2011 |
| CN102475238 (A) | Jungfeng, et al. | May 30, 2012 |
| WO2011095839 (A1) | Moreno | Aug. 11, 2011 |
| WO2010064882 (A1) | Rubens | Jun. 10, 2010 |
| CN101601639 (A) | Guoguo et al. | Dec. 6, 2009 |
| WO2008110942 (A1) | Vaizoglu, et al. | Sep. 18, 2008 |
| WO2008002116 (A1) | Bensonda, et al. | Jan. 3, 2008 |
| WO2007068757 (A1) | Msika, et al. | Jun. 21, 2007 |
| FR2877222 (A1) | Burnnier, et al. | May 5, 2006 |
| NZ523138 (A) | Horrobin | Sep. 24, 2004 |
| FR2799122 (A1); | Mathaly | Apr. 6, 2001 |
| FR2795081 (A1) | Bara, et al. | Dec. 22, 2000 |

-continued

| Foreign Pat. Documents | | |
|---|---|---|
| WO9947106 (A1) | Pierce, et al. | Sep. 23, 1999 |
| KR20000046633 (A) | Choi, et al. | Jul. 25, 2000 |
| KREP1002524 (B1) | Lerondeau, et al. | May 24, 2000 |
| EP0761203 (A1) | Maignana | Mar. 12, 1997 |
| WO9426248 (A1) | Bracco, et al | Nov. 24, 1994 |
| JPH06234644 (A) | Deibitsudo, et al, | Aug. 23, 1994 |
| CA2137001 (A1) | Elias, et al. | Jan. 6, 1994 |
| FR2694692 (A1) | Thorel, et al. | Feb. 18, 1994 |
| JPH01319414 (A) | Saimo, et al. | Dec. 25 1989 |
| FR2604624 (A1) | Papaconstantin, et al. | Apr. 8, 1988 |
| JPS6023315 (A) | Pieeruurihiyaaru | Feb. 5, 1985 |

Other Cited References

Aaron M Secrest, Kenneth D Sorensen, Carl W Hardie, Katherine M Secrest, Le T Vuong, Byron K Murray I, Kim L. O'Neill Comparative study of total antioxidant activity between the fruit Momordica cochinchinensis (gac) and its major carotenoid constituents; AAAS Conference Poster Presentation, May 2003, Bailey L H. The Garden of the Gourds. New York: The Macmillian Company, 1937:121-22.

Beilby J. Ambrosini G L et al. Serum levels of folate, lycopene, beta-carotene, retinol and vitamin E and prostate cancer. Eur J Clin Nutr. 2010 October, 64(1): 1235-8. Epub 2010, Aug. 4.

Bendich A, Olson J A. Biological actions of carotenoids FASEB J. 1989 June; 3(8):1927-32.

Boileau T. M., Boileau A. C, Erdman J. W., Bioavailability of all-trans and cis-Isomers of Lycopene, Exp Biol Med 227: 914-919, 2002.

Bulux J, Quan de Serrano J, Giuliano A, Perez R, Lopez C Y, Rivera C, Solomons N W, Canfield L M. Plasma response of children to short-term chronic β-carotene supplementation. Am J Clin Nutr 1994; 59:1369-1375.

Cooper D A. Carotenoids in health and disease: recent scientific evaluations and the consumer. JNutr. 2004 January; 134(1):221S-224S. Review.

DellaPenna D, Pogson B J. Vitamin synthesis in plants tocopherols and carotenoids. Annual Review of Plant Biology, 2006: 57:711-38, Castenmiller J J, West C E. Bioavailability and bioconversion of carotenoids. Ann Rev Ntr 1998; 18:19-38.

Combs G F J. The Vitamins, Fundamental Aspects in Nutrition and Health. San Diego, Calif.: Academic Press Inc, 1992.

Do T L Nhung Cay Thuoc va Vi Thuoc Viet Nam [Medicinal Plants and Drugs of Vietnam]. Hanoi: Nha Xuat Ban Khoa Ho via Ky Thuat, 1991.

Dueker, S. R., Vuong L. T., Faulkner B., Buchholz, B-A. Vogel, J. S., Disposition of 14C-beta-carotene following delivery with autologouts triacylglyceride-ich lipoproteins, Nuclear Instruments and Methods in Physics Research; B 259, 767-772, 2007.

Ermakov, I. V. Ermakova, M. R. Gellermann, W. Lademann, J. Noninvasive selective detection of lycopene and β-carotene in human skin using Raman spectroscopy, J Biomed Opt, 9(2), 2004.

Guichard F. Bui D S, La matiere colorante du fruit du Momordica Cochinchinnensis Spr, Annales de l'ecole Superieure de Medecine et de Pharmacie de l'Indochine 1941; V:141-42.

Herklots G A C. Vegetables in South-East Asia. London: George Allen & Unwin LTD, 1972:338-39.

Ishida B. Turner, C. Chapman M, Mckeon T. Fatty acids and carotenoids in Gac (Momordica Chochinchinensis Spreng) fruit. J Agr Food Chem. 2004; 52, 274-79

Jensen C D, Howes T W, Spiller G A, Pattison T S, Whittam J H, Sea L. Observations on the effects of ingesting cis and trans-β-carotene isomers on human serum concentrations. Nutr Rep lot 1987; 35:412-22.

Jialal L, Norkus E P, Cristol L, Grundy S M. β-carotene inhibits the oxidative modification of low-density lipoprotein Biochem. Biophys. Acta 1991; 1086:134-38.

Homnnick, D. N., C. R. Spillers, S. R. Cox, et al. Single- and Multiple-Dose-Response Relationships of Beta-Carotene in Cystic Fibrosis. J Pediatr 127, no. 3 (1995): 491-4.

Ilic D. Forbes K M, Hassed C. Lycopene for the prevention of prostate cancer, Cochrane Database Syst Rev. 2011 Nov. 9; 11:CD00807.

Lakshman M R Alpha and omega of carotenoid cleavage, J Nutr. 2004 January; 134(1):241S-245S.

Lermke, S. L., S. R. Dueker, J. R. Follett, et al. Absorption and Retinol Equivalence of Beta-Carotene in Humans Is influenced by Dietary Vitamin a Intake. J Lipid Res 44, no. 8 (2003): 1591-600.

Lopes. L. B., Reed R. A simple and rapid method to assess lycopene in multiple layers of skin samples; Biomed Chromatogr; 24(2): 154-9; 2009.

McLaren D S, Zekian B. Failure of enzymatic cleavage of β-carotene. Am J Dis Child 1971; 121:278-80.

Nguyen D V, Medicinal Plants of Vietnam, Cambodia and Laos. Westminster, Calif.: Mekong Printing, 1998:153.

Offord, E. A., J. C. Gautier, O. Avanti, et al. Photoprotective Potential of Lycopene, Beta-Carotene, Vitamin E, Vitamin C and Carnosic Acid in Uva-Irradiated Human Skin Fibroblasts, Free Radic Biol Med 32, no. 12 (2002): 1293-303.

Olsen, S. F. Effect of Vitamin a and Beta Carotene Supplementation on Women's Health. BMJ 318, no. 7183 (1999): 551-2.

Olson J A, Lakshman M R. Carotenoids conversions Methods Enzymol. 1990:189:425-32.

Olson J A. Carotenoids and human health. Arch Latinoam-Nutr. 1999 September; 49(3 Suppl 1):7S-11S. Review.

Perry L M. Medicinal Plants of East and Southeast Asia, Attributed Properties and Uses. Cambridge: The MIT Press, 1980:117.

Ross, A. B., Vuong, L. T., Ruckle R., Synal H A, Schulze-Konig T., Wertz K, Rumbeli R, Liberman R G, Skipper P L, Tannenbaum S R, Bourgeois A, Guy P A, Ensien M, Nielsen I L, Kochlar S, Richelle M, Fay L B, Williamson G. Lycopene bioavailability and metabolism in humans: an accelerator mass spectrometry study, The American Journal of Clinical Nutrition, June 2011 vol. 93 no. 6 1263-1273.

Schierle J, Bretzel W, Buhler I, Faccin N, Hess D, Steiner K, Schuep W, Content and isomeric ratios of lycopene in food and human blood plasma. Food Chem 59:459-465, 1997, Schwedhelm E, Maas R, Troost R, Böger R H. Clinical pharmacokinetics of antioxidants and their impact on systemic oxidative stress. Clin Pharmacokinet. 2003; 42(5):437-59.

Shadeque A, Baruah G. Sweet gourd: a popular vegetable of Assam. Indian Farming. 1984; 34:25-35.

Slattery M L, Jacobs D R Jr, Dyer A. Benson J, Hilner J E, Caan B J. Dietary antioxidants and plasma lipids: the Cardia Study. J Am Coll Nut 1995; 14:635-42.

Stahl W, Sies H. Uptake of lycopene and its geometrical isomers is greater from heat-processed than from unprocessed tomato juice in humans. J Nutr 122:21.61-2166, 1992

Stahl W, Heinrich U, Aust O, Tronnier H, Sies H. Lycopene-rich products and dietary photoprotection; Photochem Potobio Sci. 2006 February; 5(2):238-42. Epub 2005 Aug. 12.

Stahl W, Heinrich U, Aust O, Tronnier H, Sies H. Lycopene-rich products and dietary photoprotection, FASEB J. 1989 June; 3(8):1927-32.

Stahl W, Sies H. Photoprotection by dietary carotenoids: Concept, mechanisms, evidence and future development. Mol Nutr Food Res, 2011.

van Lieshout, M., C. E. West, and R. B. van Breemen. Isotopic Tracer Techniques for Studying the Bioavailability and Bioefficacy of Dietary, Carotenoids, Particularly Beta-Carotene, in Humans: A Review. Am J Clin Nutr 77, no. 1 (2003): 12-28.

Vo-Van-Chi. To Dien Cay Thuoc Viet Nam [A Dictionary of Medicinal Plants of Vietnam]. Ho-Chi-Minh City, Vietnam: Nha Xuat Ban Y Hoc, 1997.

Vu Dinh Trac. 100 Cay Thuoc, Van Linh Ba Chung [100 medicinal plants, highly effective for many diseases]. Hanoi: Y Hoc Viet-Nam Hoi Hun Xuat Ban, 1986:175.

Vuong, L. T., Under-utilized beta-carotene-rich crops of Vietnam. Food and Nutrition Bulletin, Vol. 21, No. 2, June 2000, pp. 173-81.

Vuang L. T., S. R. Dueker, and S. P. Murphy. Plasma Beta-Carotene and Retinol Concentrations of Children Increase after a 30-D Supplementation with the Fruit *Momordica Cochinchinensis* (Gac). Am J Clin Nutr 75, no. 5 (2002): 872-9.

Vuong, L. T., and J. C. King. A Method of Preserving and Testing the Acceptability of Gac Fruit Oil, a Good Source of Beta-Carotene and Essential Fatty Acids, Food Nutr Bull 24, no. 2 (2003): 224-30, 81.

Vuong, L. T., Buchholz, B., Dueker, S. D., AMS and in vivo phytochemical research, Nutrition Review, 62: 375-388, October 2004.

Vuong, L. T. Franke A A, Custer L. J., Murphy S. P. *Momordica cochinchinensis* Spreng. (Gac) fruit contains high β-carotene and lycopene levels; Journal of Food Composition and Analysis, February 2005, Wang X D, Krinsky N I, Benotti P N, Russell R M. Biosynthesis of 9-cis-retinoic acid from 9-cis-O-carotene in human intestinal mucosa in vitro. Arch Biochem Biophys 1998; 313:150-155.

West C E, Poortvhiet E J. The carotenoids content of foods, with special reference to develop; ping countries. Washington D.C.:USAID, 1993.

World Health Organization, Medicinal Plants in Vietnam. Hanoi: Science & Technology Publishing House, 1990: 247.

Yeum K J, Beretta G. Krinsky N I, Russell R M, Aldini G. Synergistic interactions of antioxidant nutrients in a biological model system. Nutrition 2009 July-August; 25(7-8):839-46. Epub 2009 Apr. 23.

Yeum K J, dos Anjos Ferreira A L, Smith D, Krinsky N I, Russell R M. Free Radic Biol Med. 2000 Jul. 15; 29(2): 105-14. The effect of alpha-tocopherol on the oxidative cleavage of beta-carotene.

Zhang P, Omaye S T. B-carotene and protein oxidation: effects of ascorbic acid and alpha-tocopherol; Toxicology, 2000 Apr. 20: 146(1):37-47.

What is claimed is:

1. A topical composition for treating oxidative skin damage consisting essentially of therapeutically effective amounts of gac fruit oil, avocado oil and coconut oil.

* * * * *